United States Patent

Lynn

[11] Patent Number: 4,472,977
[45] Date of Patent: Sep. 25, 1984

[54] FIXED VOLUME FLUID SAMPLER FOR PRESSURIZED PROCESS LINES

[76] Inventor: Lewis G. Lynn, 65 Hillhurst La., Rochester, N.Y. 14617

[21] Appl. No.: 416,248

[22] Filed: Sep. 9, 1982

[51] Int. Cl.³ .......................... G01N 1/10; G01N 1/20
[52] U.S. Cl. .............................. 73/863.83; 73/864.41; 73/863.73; 73/863.85; 73/864.73
[58] Field of Search .......... 73/863.83, 863.44, 863.61, 73/863.58, 863.86, 863.73, 864.73

[56] References Cited

U.S. PATENT DOCUMENTS

| 631,549 | 8/1899 | Talcott et al. | 73/863.86 X |
|---|---|---|---|
| 2,481,882 | 9/1949 | Sebald et al. | 73/863.61 X |
| 2,589,712 | 3/1952 | Langsenkemp et al. | 73/863.86 |
| 2,656,724 | 10/1953 | Cox et al. | 73/863.83 |
| 2,864,254 | 12/1958 | McDonald et al. | 73/863.73 |
| 2,973,645 | 3/1961 | Grimes et al. | 73/863.83 |
| 3,744,319 | 7/1973 | Harmes | 73/863.86 |
| 4,024,765 | 5/1977 | Abonnene | 73/863.83 |
| 4,085,618 | 4/1978 | Collins, Jr. | 73/863.73 |
| 4,147,062 | 4/1979 | Jaeger | 73/863.83 |

FOREIGN PATENT DOCUMENTS

| 1310599 | 3/1973 | United Kingdom | 73/863.83 |
|---|---|---|---|
| 579553 | 11/1977 | U.S.S.R. | 73/863.83 |

*Primary Examiner*—S. Clement Swisher
*Assistant Examiner*—Tom Noland

*Attorney, Agent, or Firm*—Shlesinger, Fitzsimmons & Shlesinger

[57] ABSTRACT

A valve containing a central recess is rotatable in a housing 180° in opposite directions to cause its recess to register selectively with identically shaped inlet and outlet ports that are formed in opposite ends, respectively, of the housing. One of a pair of circular end plates, which are secured over opposite ends, respectively, of the housing by a pair of conventional coupling members, has an axial bore that communicates at one end with the inlet port, and at its opposite end with an integral pipe that extends exteriorly of the housing, and which has an externally-threaded outer end that is adapted to be threaded into the outlet side of a conventional tee fitting, the run of which is connected in a pipe through which fluid flows under pressure. The other end plate contains a first opening connected to a drainage tube, and a second opening which is used as a vent for admitting atmospheric air to the outlet port. When the valve is turned to register with the inlet port it receives a sample of the fluid from the pipeline; and when rotated 180° in the opposite direction the fluid in its recess drains by gravity out of the outlet port to the drainage tube. The coupling members can be releasably attached to either end of the housing, so that a mounting bracket, which projects from one side of the housing, can be made to project selectively from either side of the tee to which the housing is coupled.

8 Claims, 4 Drawing Figures

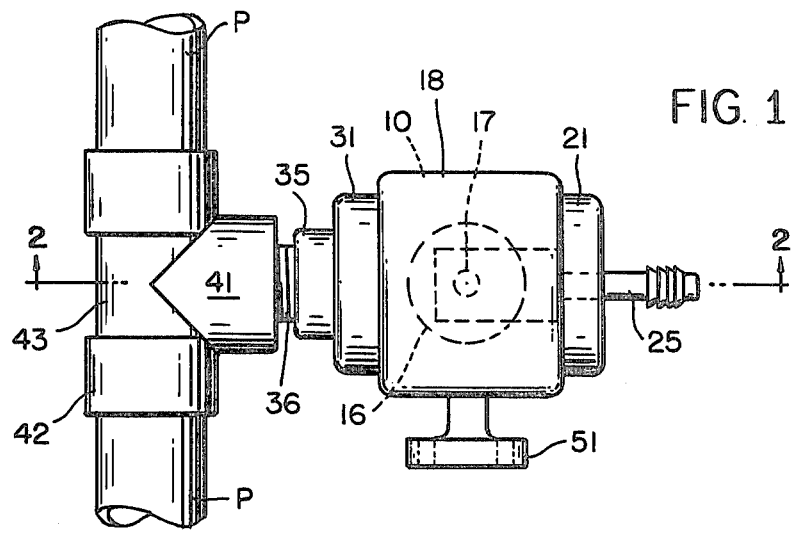
FIG. 1
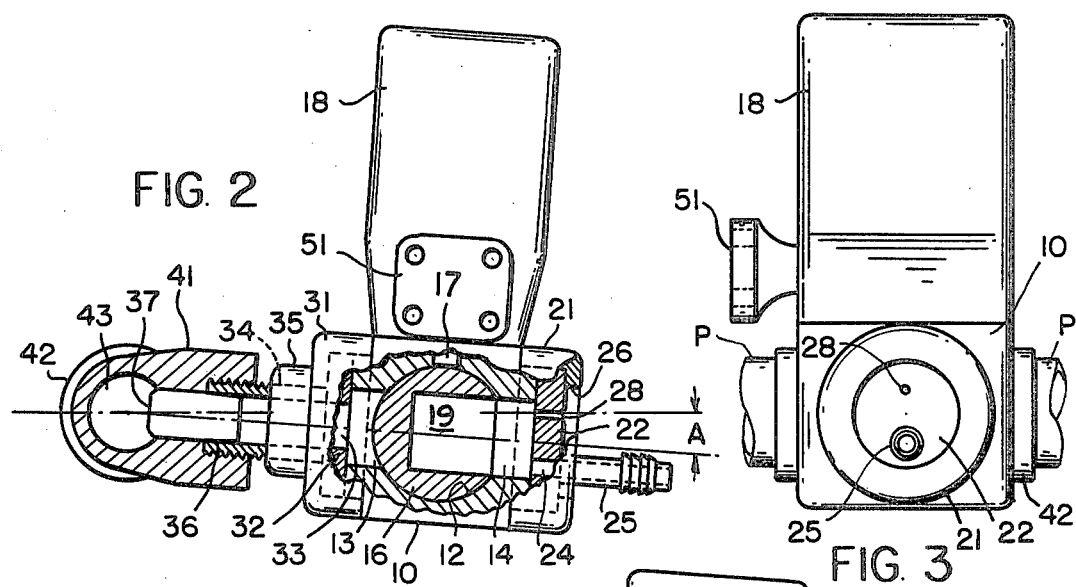
FIG. 2
FIG. 3
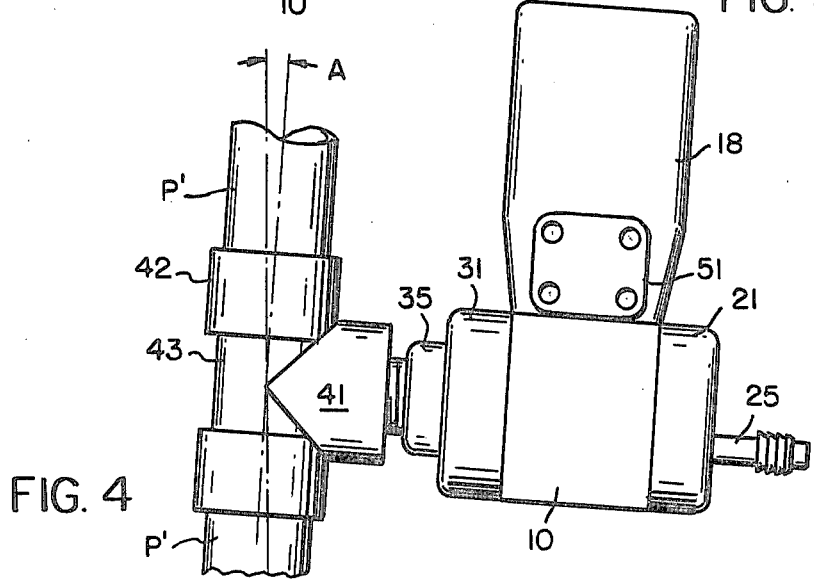
FIG. 4

FIXED VOLUME FLUID SAMPLER FOR PRESSURIZED PROCESS LINES

BACKGROUND OF INVENTION

This invention relates to fluid samplers, and more particularly to an improved sampler of the type which is adapted to be connected in pressurized process lines selectively to collect a predetermined volume of fluid from the line for sampling purposes.

There are a great many areas in which it is necessary periodically to sample a flowing fluid. Typically such fluids flow in lines which are either open to the atmosphere, or are part of a closed system which is under pressure. This invention is concerned with periodically selecting samples from a closed system of the type in which fluid flows under pressure through a pipe, or the like.

Known sampling devices of the type described include a system in which a plunger reciprocates transversely of a line in which a fluid under pressure is flowing. In so doing the sampler selects a sample from the flowing fluid and delivers it to a predetermined destination for testing purposes, or the like. These known systems have the disadvantage that they generally require both electrical and pneumatic controls for operating the sampling device, thus making the cost of the system prohibitive for many applications. These features also increase the chance of product failure resulting from either electrical or pneumatic problems. Moreover such prior devices have been rather complicated to assemble and disassemble, thus making them rather difficult to clean and repair.

It is an object of this invention, therefore, to provide an improved sampler of the type described which is relatively simple and inexpensive to manufacture and install, and yet is extremely reliable when used in the lines of pressurized systems.

Another object of this invention is to provide an improved fixed volume sampler which operates to take predetermined samples independently of any line pressure fluctuations.

Still another object of this invention is to provide an improved, electrically operated, fixed volume sampler of the type described which has a minimal amount of moving parts, and which relies solely on gravity for discharge of fluid samples from the sampler.

SUMMARY OF THE INVENTION

A valve, which has a sampling recess in one side thereof, is secured at its upper end to the shaft of a reversible motor that is selectively operable to rotate the valve 180° alternately in opposite directions in a valve housing. Opposite ends of the housing are similar in configuration, and contain sampler inlet and outlet ports, respectively, which are alternately registrable with the sampling recess in said valve. An inlet pipe, which is releasably coupled to one end of the housing, is adapted to be threaded into the leg of a tee fitting in a process pipe line to support the valve housing with its opposite end inclined slightly downwardly from the horizontal. An end plate releasably coupled to the opposite end of the housing has an air vent adjacent its upper end and a discharge pipe adjacent its lower end.

In use the motor is energized to rotate the valve 180° to a sampling position in which the recess in the valve registers with the inlet pipe. A baffle which projects from the inlet pipe into the tee fitting diverts fluid into the valve recess, after which the motor is energized to rotate the valve 180° back to a discharge position in which the valve recess registers through the housing outlet port with the discharge pipe. Air entering the vent permits the fluid in the valve recess to flow by gravity out of the downwardly inclined end of the valve housing.

THE DRAWINGS

FIG. 1 is a fragmentary plan view of a fixed volume sampler device made according to one embodiment of this invention, the sampler being shown as it appears when it is mounted on a horizontally disposed pressure line;

FIG. 2 is an enlarged, fragmentary sectional view taken generally along the line 2—2 in FIG. 1 looking in the direction of the arrows, and with portions of the sampler being shown in full;

FIG. 3 is a fragmentary end elevational view of this sampler as seen when looking toward the right end of the sampler as shown in FIG. 2; and FIG. 4 is a fragmentary elevational view of the sampler as it would appear when mounted on a vertically disposed fluid pressure line.

DETAILED DESCRIPTION OF THE PREFERRED EMBODIMENTS

Referring now to the drawings by numerals of reference, and first to FIGS. 1-3, 10 denotes a valve housing having centrally thereof a valve chamber 12, opposite ends of which communicate with aligned housing inlet and outlet ports 13 and 14, respectively. Mounted to rotate in chamber 12 about an axis that extends normal to the common axis of the ports 13 and 14 is a rotatable sampler valve 16. Valve 16 is attached at one end (its upper end in FIG. 2) to the armature or shaft 17 of a reversible electric motor of conventional design (not illustrated), which is mounted in a casing 18 that projects from the top of housing 10 as shown in the drawings. In one side thereof (the right side in FIG. 2) valve 16 has therein a large sampler recess or blind bore 19 which, as noted hereinafter, is rotatable with the valve between a first position in which its open end registers with the discharge port 14, and a second position in which its open end registers with the inlet port 13.

Releasably secured over one end of housing 10 (the right end as shown in FIG. 2) by an annular coupling member 21 is a generally disc-shaped end plate or sample discharge plate 22, the inside surface of which is sealingly secured against the right end of housing 10 to close the outer end of its port 14. Adjacent its lower end (FIG. 2) plate 22 has therethrough a small discharge duct 24, which registers at its inner end with the housing outlet port 14 adjacent the lower edge of the latter, and which opens at its outer end on the bore of a sample discharge pipe 25. Pipe 25 is fixed at its inner end to the plate 22 around the duct 24, and extends outwardly through a central opening 26 formed in the coupling member 21.

Adjacent its upper end plate 24 also has therethrough a small vent or opening 28, which connects the outlet port 14 with the opening 26 in the coupling member 21, thereby to permit the entry of atmospheric air into the upper end of the outlet duct 14, when the sampler is in use as noted hereinafter.

Releasably secured by another coupling member 31 over the opposite end of housing 10 is an annular end plate 32. Plate 32 has a plane, inner surface that is sealingly engaged against the left end of housing 10 around the outside of inlet port 13, and an axial bore 33 that communicates with a pipe 34 that projects from the outer face of plate 32 coaxially through an annular boss or hub 35 that is formed on the outer end of coupling member 31. Pipe 34 has an externally-threaded outer end 36, which projects coaxially beyond the coupling hub 35, and which has secured therein one end of a fixed baffle plate 37, the opposite end of which projects axially beyond the threaded end 36. The baffle 37 extends transversely and diametrically across the bore in pipe 34, thereby to permit fluid to flow axially through the pipe along opposite sides of the baffle.

It is to be noted that opposite ends of housing 10 are identical in configuration, each having a reduced-diameter, externally-threaded extension which is designed to be threaded into either coupling member 31 or 32. The reason for this is that casing 18 has a mounting bracket 51 projecting from one side thereof to enable the sampler, when in use, to be secured to a stationary surface near the pipe P containing the fluid that is to be sampled. Thus, if housing 10 were to be mounted 180° from its position as shown in FIG. 1, for example by securing coupling 21 over the port 13 and coupling 31 over the port 14, the sampler mounting bracket 51 would be rotated 180° from its illustrated position, thus placing it on the upside rather than the downside of tee 42 as shown in FIG. 1. This would have the effect of now making port 14 the inlet port and 13 the outlet port, but the sampler would otherwise be unchanged in operation, except that the sampling and discharge positions of ball valve 16 would be reversed.

In use, the coupling member 31 is first moved or threaded off of housing 10 from around the outside of the end plate 32 and its integral pipe extension 34. The end 36 of pipe 34 is then threaded into the side port or opening 41 in a conventional tee fitting 42, the straight section or bore 43 of which has been connected in a pressurized pipeline P. In the embodiment shown in FIGS. 1-3 pipeline P is shown to be disposed horizontally; and for this reason the end 36 of pipe 34 has been threaded into the side 41 of the tee in such a manner that the baffle 37 will be disposed in a vertical plane, as shown for example in FIG. 2. Moreover, it is essential that the end 36 be threaded into the tee 42 far enough to assure that the outer or left end of the baffle 37 (FIG. 2) will project part way into the bore 43 in tee 42, for example upwardly of about $\frac{3}{8}''$ to $\frac{1}{2}''$. Thereafter the coupling 31 is utilized sealingly to secure either end of the housing 10 against the face of the end ring 32.

Assuming that coupling member 31 has been threaded over the housing 10 as shown in FIG. 2, the end plate 22 is thereafter secured over the opposite end of the housing by means of coupling member 21, care being taken to adjust plate 22 so that its outlet pipe 25 is located at its lowermost point relative to the axial center line of housing 10. Also at this time it is important to assure that the tee 42 is adjusted on pipe P in such manner that the axial centerline of pipe 34 and valve chamber 12 is included slightly downwardly to the horizontal, as denoted for example by the angle A in FIG. 2. In practice this angle should be about 3° to 5° for a purpose noted hereinafter.

By electrical controls which form no part of this invention, the reversible motor in casing 18 is periodically energized to rotate the shaft 17 to 180° in opposite directions about its axis. This causes valve 16 intermittently to be rotated 180° from its position as shown in FIG. 2, in which case its recess or pocket 19 will have its open end placed in registry with the inner end of port 13, and its closed end placed over and in closing relation to the inner end of the outlet 14. When this occurs the fluid flowing in pipe P will be deflected by the projecting end of baffle 37 through the pipe 34 and the inlet port 13 into the valve recess 19 until the latter is almost filled. Since at this stage the axis of the recess 19 is inclined slightly to the horizontal, the inner end of the recess is slightly lower than its outer end, whereby air in the chamber or recess 19 is allowed to dissipate outwardly into the process line of pipe P at the same time that fluid from the line is flowing into the recess 19. This prevents any undesirable air lock or blockage from occurring in the sampler.

Shortly after the valve 16 has been rotated to its sampling position, the motor in casing 18 is once again energized by means which form no part of this invention, thereby causing the motor shaft 17 to rotate valve 16 180° back to its starting or sample discharge position as illustrated in FIG. 2. When this occurs the open end of recess 19 registers with the outlet port 14, the outlet duct 24 and the outlet pipe 25, at the same time that air from the exterior of the sample is allowed to enter the recess 19 through the vent 28. Because of the slight downwardly directed angle of the sampler, the fluid in recess 19 therefore slowly drains out of the pipe 25 and into a tube or any other conventional means (not illustrated) for conveying the sample to the desired location. This completes one sampling cycle.

FIG. 4 illustrates schematically the manner in which the casing 10 should be mounted for sampling fluid conveyed under pressure in a vertically disposed pipe, or nearly vertically disposed pipe, P'. In such case it is desirable that a section of the pipe P', namely that section including the tee 42, be inclined slightly to the vertical, for example at the same angle A as described in connection with the first embodiment. This has the effect of causing the axis of casing 10 and pipe 34 to be inclined to the horizontal approximately to the same extent as when used in the manner described in connection with the embodiment shown in FIGS. 1 to 3. When used in this manner, it is important that the pipe 34 and its associated end plate 32 be located in such a position that the attached baffle 37 is disposed in a nearly horizontal plane, as distinguished from the vertical plane in which it is positioned when the sampler is used as shown in FIG. 2. The obvious reason is that, when the fluid is flowing vertically, the baffle 37 should lie generally in a horizontal plane so as to be most effective in deflecting fluid into the chamber 19 in valve 16.

From the foregoing it will be apparent that the present invention provides relatively simple and inexpensive means for quickly and easily sampling fluid which is flowing at a high pressure in a given process line. Simply by periodically energizing the motor in the housing 18, the valve 16 can be rotated 180° first in one direction and then in another, thereby to remove a sample of fluid from the associated pipe line. By tilting the mechanism slightly to the horizontal, dissipation of air from within the chamber 19 is enhanced during the filling of the sample chamber; and the discharge of the fluid from the sample chamber after return of the valve 16 to its discharge position is effected by gravity, and obviates the need for employing a separate purging or transfer device for removing the sample fluid from the valve 16. The use of the baffle 37 assures an ample supply of fluid whenever valve 16 is rotated to its sampling position, and also constantly circulates part of the fluid in pipe P into pipe 34 and port 13, thereby assuring the presence of a fresh sample when valve 16 swings to its sampling position. Moreover, by using a casing 10 which is similar in configuration at each end, it is possible selectively to place the mounting bracket 51 to one side or the other of the associated tee inlet 41, thereby easing the installation of the device. Also, by employing the removable couplings 21 and 31 for releasably securing the end plates over opposite ends of the housing 10, it is a relatively simple matter to dismantle the unit to gain access to the valve 16 and associated parts for cleaning or repairing.

Although not illustrated in detail herein, it will be apparent that conventional sealing devices, such as resilient O-rings or the like are employed between confronting surfaces which are to be sealingly connected one to the other. Also, although the motor in casing 18 has not been illustrated and described in detail, it will be understood that this particular part of the unit is of conventional design, and need only be able to rotate the shaft 17 selectively in opposite directions for 180° intervals. Moreover, it will be apparent that the exact shape of the valve 16 in its associated sampling chamber 19 could be changed without altering this invention. Furthermore, although the invention has been illustrated and described in detail in connection with only certain embodiments thereof, it will be apparent that it is capable of still further modifications, and that this application is intended to cover any such modifications as may fall within the scope of one skilled in the art, or the appended claims.

What I claim is:

1. A fixed volume fluid sampler, comprising
    a housing,
    a sampling valve having a recess with an open end and a closed end mounted in a chamber in said housing for rotation between a first position in which the open end of said recess in said valve registers with a fluid outlet port in one end of said housing, and a second position in which the open end of said recess registers with a fluid inlet port in the opposite end of said housing,
    first coupling means for releasably connecting said opposite end of the housing to a pipe containing fluid under pressure, and with said inlet port in communication with the fluid in said pipe,
    second coupling means for releasably connecting a drainage tube to said one end of said housing and with the bore in said tube communicating with said outlet port, and
    means for selectively rotating said valve momentarily from said first to said second position, and then back to said first position,
    said first coupling means including baffle means disposed to direct a sample of fluid from said pipe to said recess in said valve, when the latter is in its second position,
    and
    said second coupling means including means for causing said sample of fluid in said valve recess to drain by gravity out of said open end of said recess and through said tube to the exterior of said housing, when said valve is returned to said first position.

2. A fixed volume fluid sampler as defined in claim 1, including a mounting bracket for said housing projecting from one side thereof, and opposite ends of said housing being similar in configuration, whereby each of said coupling means may be releasably connected selectively to either end of said housing, thereby to permit said bracket to be positioned selectively in one of at least two different positions relative to the pipe to which the housing is connected.

3. A fixed volume fluid sampler comprising
    a housing,
    a sampling valve mounted in a chamber in said housing for rotation between a first position in which a recess in said valve registers with a fluid outlet port in one end of said housing, and a second position in which said recess registers with a fluid inlet port in the opposite end of said housing,
    first coupling means for releasably connecting said opposite end of the housing to a pipe containing fluid under pressure, and with said inlet port in communication with the fluid in said pipe,
    second coupling means for releasably connecting a drainage tube to said one end of said housing and with the bore in said tube communicating with said outlet port, and
    means for selectively rotating said valve momentarily from said first to said second position, and then back to said first position,
    said first coupling means including baffle means disposed to direct a sample of fluid from said pipe to said recess in said valve, when the latter is in its second position,
    and
    said second coupling means including means for causing said sample of fluid in said valve recess to drain by gravity out of said tube, when said valve is returned to said first position,
    said first coupling means further including a tubular member having a circumferential shoulder on one end, and an externally-threaded section on its opposite end disposed to be threaded into a tee fitting on said pipe, and
    a first coupling member for releasably securing said shoulder over said opposite end of said housing with the bore in said tubular member communicating with said inlet port,
    said baffle means comprising a flat bar secured at one end in the bore of said tubular member to extend in a diametral plane transversely thereof, and projecting at its opposite end out of said tubular member a distance sufficient to cause it to project part way into the bore of said tee that extends coaxially of said pipe.

4. A fixed volume fluid sampler comprising
    a housing,
    a sampling valve mounted in a chamber in said housing for rotation between a first position in which a recess in said valve registers with a fluid outlet port in one end of said housing, and a second position in which said recess registers with a fluid inlet port in the opposite end of said housing,
    first coupling means for releasably connecting said opposite end of the housing to a pipe containing fluid under pressure, and with said inlet port in communication with the fluid in said pipe,
    second coupling means for releasably connecting a drainage tube to said one end of said housing and with the bore in said tube communicating with said outlet port, and means for selectively rotating said valve momentarily from said first to said second position, and then back to said first position, said first coupling means including baffle means disposed to direct a sample of fluid from said pipe to said recess in said valve, when the latter is in its second position, and said second coupling means including means for causing said sample of fluid in said valve recess to drain by gravity out of said tube, when said valve is returned to said first position, said second coupling means further including a circular plate having said drainage tube projecting from one side thereof and registering with a discharge opening in said plate, and a second coupling member for releasably securing said plate over said one end of said housing with said discharge opening in said plate communicating with said outlet port adjacent the lower edge thereof, and with said discharge tube extending exteriorly of said housing through a central opening in said second coupling member, said plate having therethrough a second opening smaller in diameter than said discharge opening, and disposed to register at one end with said outlet port adjacent the upper edge thereof, and at its opposite end with the central opening in said second coupling member to vent said outlet port during drainage of fluid from said valve recess.

5. A fixed volume sampler adapted to be connected to the outlet of a tee fitting which has its run connected in a pipe through which fluid flows under pressure, comprising a housing having therein spaced inlet and outlet ports, a sampling valve movably mounted in a chamber located in said housing between said ports, and having therein a sampling recess with an open end and a closed end, the open end of which is registrable selectively with said ports, means for selectively moving said valve to a first position in which said open end of its recess registers with said inlet port, and then to a second position in which said open end registers with said outlet port, means for releasably connecting the inlet port in said housing to the outlet of a tee fitting the run of which is connected in the pipe containing fluid flowing under pressure, whereby fluid from said pipe enters the open end of said recess in said valve when the latter is in said first position, and means connected to the outlet port in said housing and defining a pair of spaced openings one of which communicates through said outlet port with said open end of said recess adjacent one side thereof to admit atmospheric air to said recess, when said valve is in its second position, and the other of which communicates through said outlet port with the open end of said recess adjacent the opposite side thereof to allow fluid to flow by gravity from said recess, when said valve is in its second position.

6. A fixed volume sampler adapted to be connected to the outlet of a tee fitting which has its run connected in a pipe through which fluid flows under pressure, comprising a housing having therein spaced inlet and outlet ports, a sampling valve movable mounted in a chamber located in said housing between said ports, and having therein a sampling recess registrable selectively with said ports, means for selectively moving said valve to a first position in which its recess registers with said inlet port, and then to a second position in which its recess registers with said outlet port, means for releasably connecting the inlet port in said housing to the outlet of a tee fitting the run of which is connected in a pipe containing fluid flowing under pressure, whereby fluid from said pipe enters the recess in said valve when the latter is in said first position, and means connected to the outlet port in said housing and defining a pair of spaced opening one of which communicates through said outlet port with said recess adjacent the upper end thereof to admit atmospheric air to said recess, when said valve is in its second position, and the other of which communicates through said outlet port with the lower end of said recess to allow fluid to flow therefrom by gravity, when said valve is in its second position, said means for releasably connecting the inlet port to said tee fitting comprising a tubular mounting member releasably attached at one end to said housing over said inlet port and having on its opposite end an externally-threaded portion disposed to be threaded into said tee outlet, and means projecting from said externally-threaded end of said mounting member and disposed to project into the run section of said tee positively to divert fluid from said pipe into the inlet in said housing.

7. A fixed volume sampler as defined in claim 6, including a bracket fixed to said housing adjacent one side thereof and disposed to support the latter with said outlet port and valve recess inclined slightly downwardly from the horizontal, said tubular mounting member being releasably attachable selectively to either end of said housing to enable the positioning of said bracket selectively to one side or the other of the tee outlet in which said tubular member is threaded.

8. A fixed volume sampler as defined in claim 6, wherein said projecting means comprises a flat bar fixed at one end in the bore of said tubular member to extend in a diametral plane transversely thereof, and projecting at its opposite end beyond said opposite end of the tubular member to enter partway into the run of said tee, and means adjustably securing said tubular member to said one end of said housing and operable to permit placement of said projecting end of said bar transversely of the run in the tee on which the sampler is mounted.

* * * * *